(12) United States Patent
Atwal et al.

(10) Patent No.: US 6,664,250 B2
(45) Date of Patent: Dec. 16, 2003

(54) LACTAM DERIVATIVES AS ANTIARRHYTHMIC AGENTS

(75) Inventors: Karnail S. Atwal, Newtown, PA (US); Saleem Ahmad, Wall, NJ (US); Francis N. Ferrara, Martinsville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/267,466

(22) Filed: Oct. 9, 2002

(65) Prior Publication Data
US 2003/0114438 A1 Jun. 19, 2003

Related U.S. Application Data

(63) Continuation of application No. 09/862,203, filed on May 22, 2001, now abandoned, which is a division of application No. 09/231,678, filed on Jan. 14, 1999, now Pat. No. 6,262,068, which is a continuation-in-part of application No. 09/008,948, filed on Jan. 20, 1998, now abandoned.

(51) Int. Cl.$^7$ .................. C07D 487/00; A61K 31/55
(52) U.S. Cl. ........................ 514/212.03; 540/523
(58) Field of Search ................. 540/523; 514/212.07

(56) References Cited

U.S. PATENT DOCUMENTS

| | | | | |
|---|---|---|---|---|
| 4,746,657 A | * | 5/1988 | Cale, Jr. ................. | 514/215 |
| 4,871,735 A | | 10/1989 | Helder et al. ............ | 514/213 |
| 5,132,311 A | | 7/1992 | Liang ..................... | 514/307 |

FOREIGN PATENT DOCUMENTS

| | | |
|---|---|---|
| EP | 548934 | 6/1993 |
| WO | WO93/04061 | 4/1993 |
| WO | WO95/14471 | 1/1995 |
| WO | WO9511228 | 4/1995 |
| WO | WO96/05839 | 2/1996 |

OTHER PUBLICATIONS

Reiffen et al . J.Med.Chem.(1990), vol. 33 (12), 3229.
Zhao et al. Org. Prep. Proced.Int.(1997) vol. 29 (2), 185–194.
Shanker et al. Indian J. Chem., Sect. B (1993) vol. 32B (12) 1209–1213.

Selnick, H.G. et al. J. Med. Chem., (1997) vol. 40 (24) 3865–3868.
Nair, L.A. et al, Cardiovascular Drugs and Therapy 1997, vol. 11, 149–167.
Erez, et al, Journal of Medicinal Chemistry, 1978, vol. 21, No. 9.

* cited by examiner

Primary Examiner—Bruck Kifle
(74) Attorney, Agent, or Firm—Jonathan N. Provoost

(57) ABSTRACT

Lactam derivatives of the formula

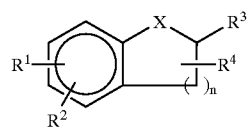

where

X is —C(=O)NR$^{3'}$—, —NR$^{3'}$C(=O)—, —C(=NCN)NR$^{3'}$—, —NR$^{3'}$C(=NCN)—, —CH$_2$NR$^{3'}$—, —CH(alkyl)NR$^{3'}$—, —CH(COOalkyl)NR$^{3'}$—, —CH(CH$_2$OH)NR$^{3'}$—, —C(CH$_2$Oalkyl)—;

R$^1$ is halo, alkyl, cycloalkyl, alkyl(cycloalkyl), aryl, (aryl)alkyl, (aryl)alkenyl, (aryl)alkynyl, O-alkyl, O-alkenyl, O-aryl, O-alky(aryl), O-alkyl(heterocyclo), COO-alkyl, C)-alkyl, CO-amino, CO-substituted amino, alkyl-CO-amino, alkyl-CO-substituted amino, NHCO-alkyl, NHCO-aryl, NHCO-alkyl(aryl), NHCO-alkyl(heterocyclo), N(alkyl)CO-alkyl, N(alkyl)CO-aryl, N(alkyl)CO-heterocyclo, N(alkyl)CO-alkyl(aryl), N(alkyl)CO-alkyl(heterocyclo);

R$^2$ is hydrogen, alkyl, halo, aryl, (aryl)alkyl, O-alkyl, amino, substituted amino;

R$^3$ and R$^{3'}$ are the same or different and are independently selected from hydrogen, alkyl or alkyl(aryl);

R$^4$ which can be bonded to a ring carbon or nitrogen, is selected from hydrogen, alkyl, alkenyl, alky(aryl), alkyl(heterocyclo), cycloalkyl, alkyl(cycloalkyl), alkyl-(amino), alkyl-(substituted amino), alkyl-NHCO(alkyl), alkyl-NHCO(aryl), alkyl-NHCO(heterocyclo), alkyl-NHCO(alkylaryl), alkyl-NHCO(alkylheterocyclo); and n is an integer of 0 to 2. These compounds have been found to be useful in the treatment of arrhythmia.

3 Claims, No Drawings

LACTAM DERIVATIVES AS ANTIARRHYTHMIC AGENTS

This application is a Continuation of Ser. No. 09/862,203 filed May 22, 2001, now abandoned, which is a Divisional of Ser. No. 09/231,678 filed Jan. 14, 1999, now issued as U.S. Pat. No. 6,262,068, which is a continuation-in-part of application Ser. No. 09/008,948 filed Jan. 20, 1998, now abandoned.

BRIEF DESCRIPTION OF THE INVENTION

This invention is concerned with compounds of the formula

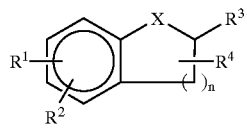

where
X is —C(=O)NR$^{3'}$—, —NR$^{3'}$C(=O), —C(=NCN)NR$^{3'}$—, —NR$^{3'}$C(=NCN)—, —CH$_2$NR$^{3'}$—, —CH(alkyl)NR$^{3'}$—, —CH(COOalkyl)NR$^{3'}$—, —CH(CH$_2$OH)NR$^{3'}$—, —C(CH$_2$Oalkyl)—;

R$^1$ is halo, alkyl cycloalkyl, alkyl(cycloalkyl), aryl, (aryl)alkyl, (aryl)alkenyl, (aryl)alkynyl, O-alkyl, O-alkenyl, O-aryl, O-alky(aryl), O-alkyl(heterocyclo), COO-alkyl, CO-alkyl, CO-amino, CO-substituted amino, alkyl-CO-amino, alkyl-CO-substituted amino, NHCO-alkyl, NHCO-aryl, NHCO-alkyl(aryl), NHCO-alkyl(heterocyclo), N(alkyl)CO-alkyl, N(alkyl)CO-aryl, N(alkyl)CO-heterocyclo, N(alkyl)CO-alkyl(aryl), N(alkyl)CO-alkyl(heterocyclo);

R$^2$ is hydrogen, alkyl, halo, aryl, (aryl)alkyl, O-alkyl, amino, substituted amino;

R$^3$ and R$^{3'}$ can be the same or different and are independently selected from hydrogen, alkyl, alkyl(aryl);

R$^4$ which can be bonded to a ring carbon or nitrogen, is selected from hydrogen, alkyl, alkenyl, alky(aryl), alkyl(heterocyclo), cycloalkyl, alkyl(cycloalkyl), alkyl-(amino), alkyl-(substituted amino), alkyl-NHCO(alkyl), alkyl-NHCO(aryl), alkyl-NHCO(heterocyclo), alkyl-NHCO(alkylaryl), alkyl-NHCO(alkylheterocyclo); and n is an integer of 0 to 2.

These compounds are useful in the treatment of arrhythmia. The invention is also concerned with pharmaceutical compositions comprising one or more of the novel compounds as an active antiarrhythmic agent either alone or in combination with other cardiovascular agents such as a B-blocker or other antiarrhythmic agent; and a method of treating arrhythmia by administration of one of the novel compounds or compositions thereof to a patient in need of such treatment.

DETAILED DESCRIPTION OF THE INVENTION

Definition of Terms

Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 8 carbon atoms, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like; as well as such groups substituted by, one or more substituents such as halo, alkoxy, amino, substituted amino, aryl, cycloalkyl, hydroxy, heterocyclo, alkanoylamino, arylcarbonylamino, nitro, cyano, thiol, alkylthio and the like.

The term "alkoxy" refers to alkyl-O—.

The term "alkylthio" refers alkyl-S—.

The term "alkenyl" refers to any of the above alkyl groups further containing at least one carbon to carbon double bond.

The term "alkynyl" refers to any of the above alkyl groups further containing at least one carbon to carbon triple bond.

The term "alkanoyl" refers to alkyl-C(O)—.

The term "cycloalkyl" refers to saturated cyclic hydrocarbon groups containing 3 to 8 ring carbons optionally substitued with one or more substituents such as alkyl or hydroxy.

The term "halogen" or "halo" refers to chlorine, bromine, iodine and fluorine.

The term "aryl" refers to monocyclic or bicyclic aromatic hydrocarbon groups having 6 to 12 carbon atoms in the ring portion, such as phenyl, 1-naphthyl, 2-naphthyl, phenanthrene or dihydrophenanthrene; or such groups substituted with one or more substituents such as alkyl, alkylthio, alkoxy, halo, nitro, cyano, hydroxy, amino, substituted amino, phenyl, —C(O)-phenyl, substituted phenyl, —C(O)-substituted amino, heterocycle, carboxylic acid or carboxylic ester.

The term "aryl" also includes those groups listed above fused to a five- or six-membered ring which optionally contains an oxygen, sulfur or nitrogen atom. The five- or six-membered ring may further optionally be substituted with for example, alkyl or -phenyl-CF$_3$.

The term "heterocyclo" or "hetero" refers to fully saturated or unsaturated rings of five or six atoms containing one or two oxygen and/or sulfur atoms and/or one to four nitrogen atoms provided that the total number of hetero atoms in the ring is four or less. Exemplary monocyclic heterocyclo groups include 2- and 3-thienyl, 2- and 3-furyl, 2-, 3- and 4-pyridyl and imidazolyl.

The term heterocyclo or hetero also includes bicyclic rings wherein the five- or six-membered ring containing oxygen and/or sulfur and/or nitrogen atoms as defined above is fused to a benzene ring and the bicyclic ring is attached by way of an available atom.

Exemplary bicyclic hetero groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl and 4-, 5-, 6- or 7-benzofuranzanyl.

The term heterocyclo or hetero also includes such monocyclic and bicyclic rings wherein an available atom is substituted by one or more substituents such as alkyl, aryl, alkylthio, alkoxy, halo, nitro, keto, cyano, hydroxy, azo, oxo, thiazo, amino, substituted amino, carboxylic acid, carboxylic ester, or alkoxy further substituted with a carboxylic acid or a five- to eight-membered ring optionally containing 1 to 4 heteroatoms selected from oxygen, nitrogen and sulfur, optionally substituted by groups such as alkyl or halogen.

The term "substituted amino" refers to a group of the formula —NZ$^1$Z$^2$ wherein Z$^1$ is hydrogen, alkyl, cycloalkyl, aryl, morpholinylalkyl, heterocyclo or (heterocyclo)alkyl and $Z^2$ is hydrogen, alkyl, cycloalkyl or aryl further substituted with a carboxylic acid or carboxylic ester, provided that when $Z^1$ is hydrogen, then $Z^2$ is other than hydrogen; or $Z^1$ and $Z^2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, aryl or hydroxy.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compound I with the desired ion in a medium in which the salt precipitates or in an aqueous medium followed by evaporation. Other salts can be formed as known to those having ordinary skill in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compound I in an equivalent amount of the acid in a medium in which the salt precipitates or in an aqueous medium followed by evaporation.

In addition, zwitterions ("inner salts") may be formed.

A compound of the formula I may also have prodrug forms. Any compound that will be converted in vivo to provide the bioactive agent (i.e., the compound of formula I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985);

b) *Methods in Enzymology*, Vol. 42, 309–396, edited by K. Widder et al. (Academic Press, 1985);

c) *A Textbook of Drug Design and Development*, edited by Krogsgaard-Larsen and H.

Bundgaard, Chapter 5, "Design and Application of Prodrugs," by H.

Bundgaard, 113–191 (1991);

d) *Advanced Drug Delivery Reviews*, H. Bundgaard, 8, 1–38 (1992);

e) *Journal of Pharmaceutical Sciences*, H. Bundgaard et al., 77, 285 (1988); and f) *Chem Pharm Bull*, N. Kakeya et al., 32, 692 (1984).

It should further be understood that solvates (e.g., hydrates) of the compounds of formula I are also within the scope of the present invention. Methods of solvation are generally known in the art.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The below described processes can utilize racemates, enantiomers or diastereomers as starting materials. When diastereomeric products are prepared, they can be separated by conventional methods for example, chromatographic or fractional crystallization.

Use and Utility

The compounds of formula I are useful in the treatment of arrhythmia. More specifically, the compounds of the present invention have the pharmacological properties required for the antiarrhythmic agents of Class III.

Class III agents increase myocardial refractoriness via a prolongation of cardiac action potential duration. Theoretically, prolongation of the cardiac action potential can be achieved by enhancing inward currents (i.e. $Na^+$ or $Ca^{2+}$ currents; hereinafter $I_{Na}$ and $I_{Ca}$ respectively) or by reducing outward repolarizing potassium ($K^+$) currents. The delayed rectifier ($I_K$)$K^+$ current is the main outward current involved in the overall repolarization process during the action potential plateau, whereas the transient outward ($I_{to}$) and inward rectifier ($I_{K1})_K^+$ current are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating).

Most Class III agents that are known to be in development predominantly block $I_{Kr}$. These agents have a potential liability in that they have an enhanced risk of proarrhythmia at slow heart rates. The compounds of the present invention prolong the mycocardial action potential in vitro without a significant depression of the Vmax and with the prolongation of Qtc-interval in anesthetized dogs. In addition the compounds of the present invention selectively block $I_{Ks}$. The preferred compounds of the present invention are those which have selectivity of $I_{Ks}$:$I_{Kr}$ greater than or equal to 5.

The compounds of the present invention are effective in treating and preventing all types of arrhythmias including ventricular and atrial (supraventricular) arrhythmias. The compounds of the present invention are especially useful to control reentrant arrhythmias and prevent sudden death due to the ventricular fibrillation.

In the novel method of this invention of treating arrhythmia, a novel compound or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

The novel compounds of this invention can be administered as the sole active ingredient or in combination with other antiarrhythmic agents or other cardiovascular agents.

The compounds, or pharmaceutically acceptable salts thereof, of the present invention, in the described dosages, are administered orally, intraperitoneally, subcutaneously, intramuscularly, transdermally, sublingually or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

Preferred Moieties

The preferred compounds of the present invention are those compounds of formula I where:

X is —C(=O)NR$^{3'}$—, —NR$^{3'}$C(=O)—, —CH(CH$_2$OH)NR$^{3'}$—,

R$^1$ is alkoxy;

R$^2$ is hydrogen;

R$^3$ and R$^{3'}$ are the same or different and are independently selected from hydrogen or alkyl;

R$^4$ is hydrogen, alkyl(heterocyclo), alkyl(substituted amino); and n is an integer of 0 to 2.

Process of Preparation

The compounds of the instant invention can be obtained by methods exemplified by the following descriptions.

Compounds of formula IA, which are compounds of formula I wherein R$^3$ is hydrogen, n=0–2 and R$^4$ is alkyl-substituted amino, can be prepared according to Scheme 1.

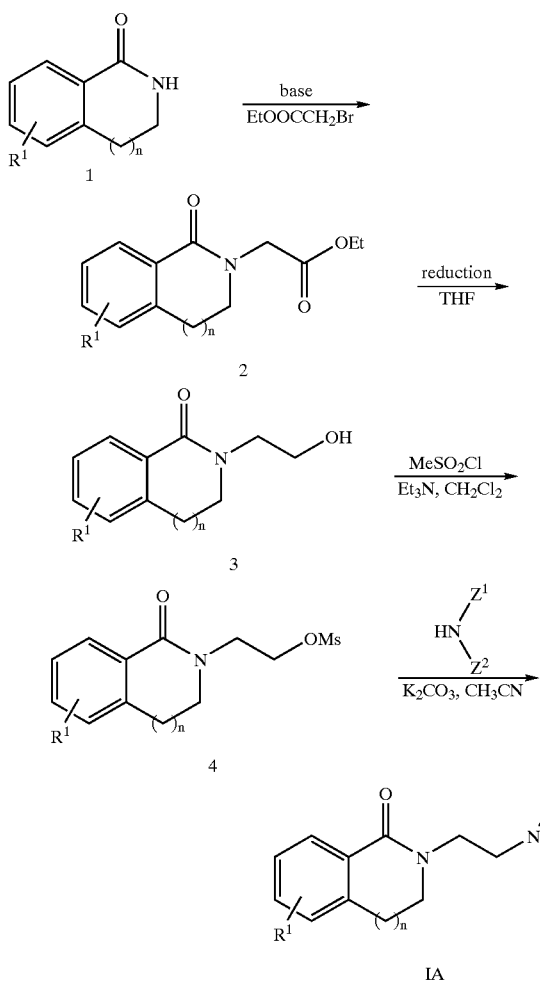

The compound of formula 1 is alkylated with ethyl bromoacetate in the presence of a base and the resulting compound 2 is reduced with a reducing agent such as LiBH$_4$. The alcohol in product 3 is converted to a leaving group (e.g., mesylate, halide etc.) and displaced with an amine to provide the target compound IA.

Compounds of formula 1 are known in the literature (e.g., J. Chem. Soc., 1969, p 183) and other reagents employed in Scheme I are either commercially available or they can be prepared by literature methods.

Compounds of formula IA, can also be prepared according to Scheme 2.

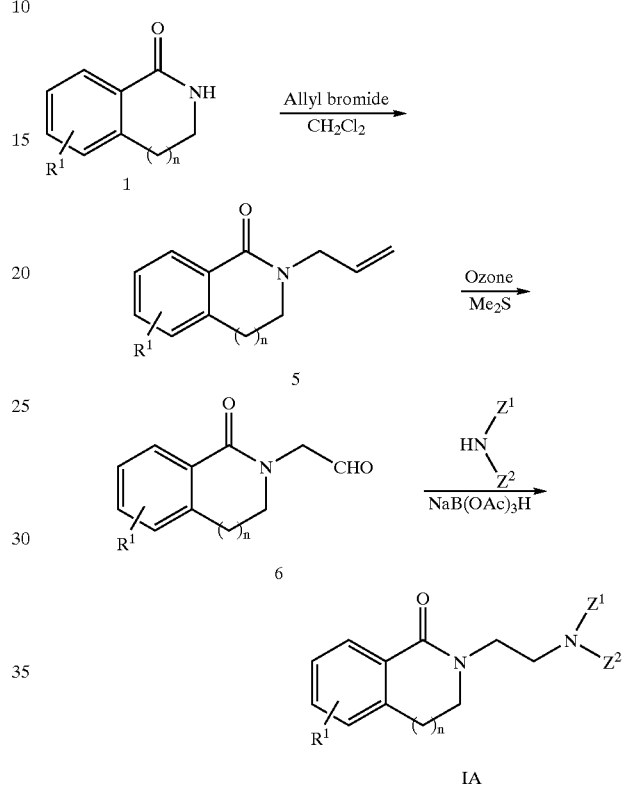

The compound of formula 1 is alkylated with allyl bromide in the presence of a base and the resulting compound 5 is treated with ozone followed by NaB(OAc)$_3$H to provide the aldehyde 6. Reductive amination of 6 with an amine of formula Z$^1$Z$^2$NH provides the requisite compounds of formula IA.

The reagents employed in Scheme 2 are either commercially available or they can be prepared by literature methods.

Compounds of formula IC and ID are compounds of formula I wherein X is —C(=O)N or —NC(=O)— and n=0–1 and can be prepared according to Scheme 3.

Scheme 3

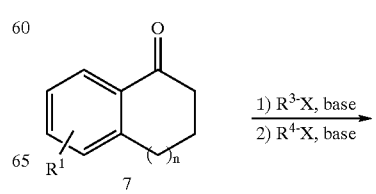

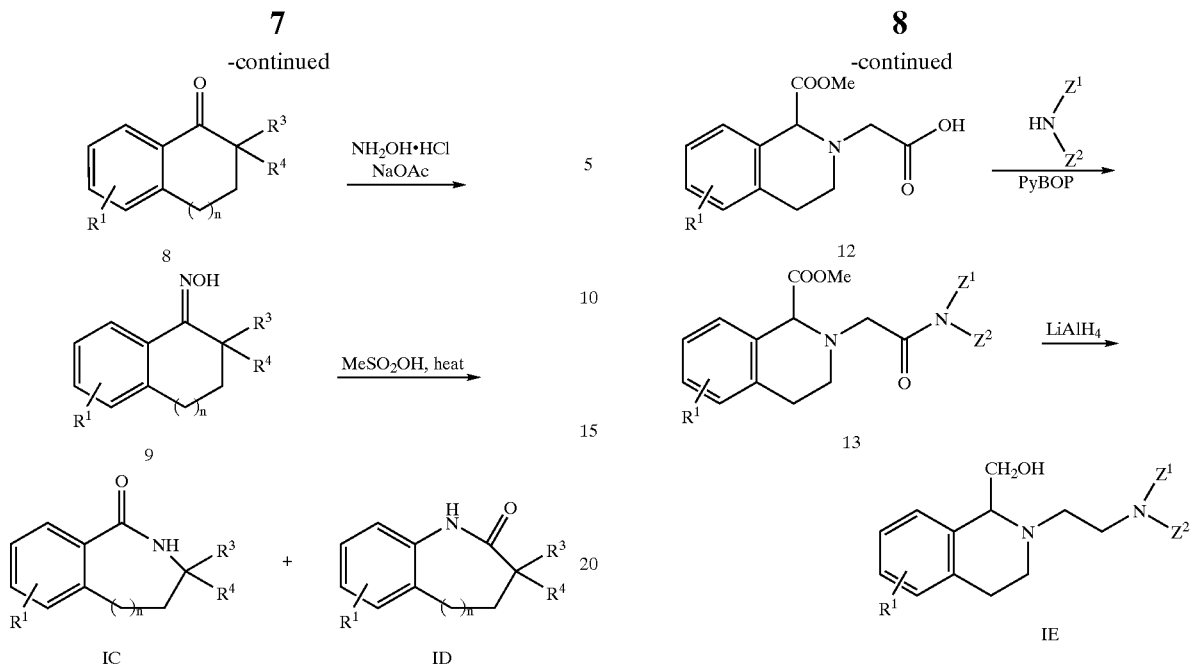

The ketone of formula 7 is alkylated with a suitable alkylating agent once or twice (depending on the substituents $R^3$ and $R^4$). The resulting compound 8 is converted to a mixture of oximes 9 by treatment with hydroxyl amine hydrochloride and sodium acetate. The oxime 9 undergoes Beckmann rearrangement in methanesulfonic acid to provide the desired products IC and ID. Alternatively, compounds IC and ID can be directly prepared from ketone 8 by treatment with sodium azide in the presence of sulfuric acid. The ratio of IC to ID depends on the substituents $R^3$ and $R^4$ and the reaction conditions employed.

Compounds of formula 7 are commercially available or they can be prepared by methods known in the literature methods.

Compounds of formula IE which are compounds of formula I wherein X is —C(CH$_2$OH), $R^3$ is hydrogen, n=1 and $R^4$ is alkyl-substituted amino, can be prepared from 1 as described in Scheme 4.

Scheme 4

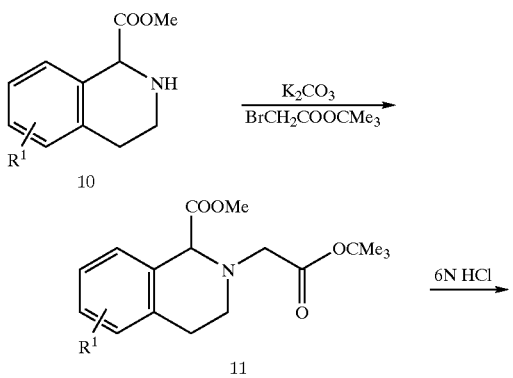

The amine in 10 is alkylated with an appropriate alkylating agent (e.g., ter-Butylbromoacetate) in the presence of a base (e.g., potassium carbonate). The ter-butyl group in 11 can be removed by acid treatment and the resulting acid 12 is coupled with an amine of formula $Z^1Z^2$NH under standard conditions. The amide in 13 is reduced to provide compounds of formula IE.

Compounds of formula 10 are described in the literature (W. K. Anderson, H. L. McPherson, J. S. New and A. C. Rick, Journal of Medicinal Chemistry, Vol. 27, p. 1321, 1984) and other reagents used in Scheme 4 are either commercially available or they can be prepared according to methods described in the literature.

Various reactive groups (e.g., amine, hydroxyl) that can potentially interfere with the reaction sequence described in Schemes 1–4, are protected with appropriate protecting groups such as those described in the literature. The protecting groups are removed after the requisite transformations.

EXAMPLES

The following examples and preparations describe the manner and process of making and using the invention and are illustrative rather than limiting. It should be understood that there may be other embodiments which fall within the spirit and scope of the invention as defined by the claims appended hereto.

Example 1

3,4-Dihydro-6-methoxy-2-[2-(4-phenyl-1-piperidinyl)ethyl]-1(2H)-isoquinolinone, Monohydrochloride

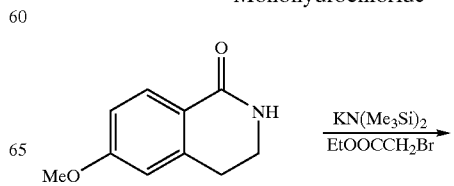

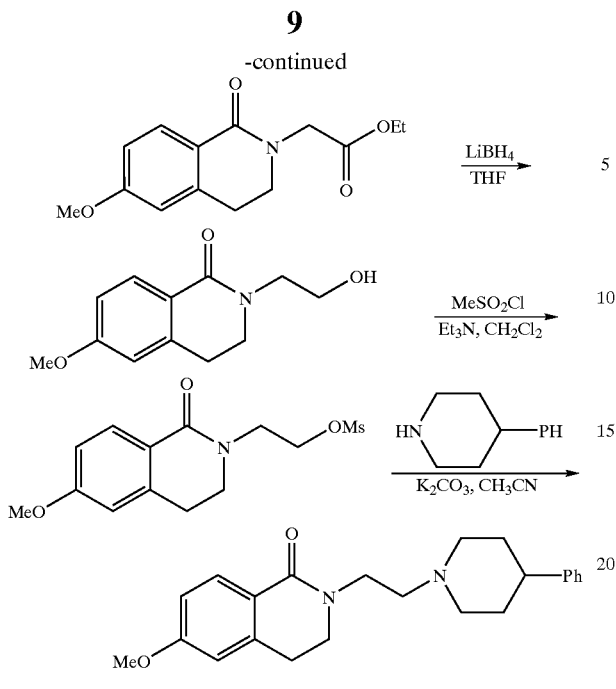

A. 3,4-Dihydro-6-methoxy-2(1H)-isoquinolineacetic Acid Ethyl Ester

To a solution of 3,4-dihydro-6-methoxy-1(2H)-isoquinolinone (852 mg, 4.81 mmol, prepared according to J. Chem. Soc., 1969, p 183) in THF (45 mL) at −78° C. was added 0.5M potassium hexamethyldisilazide (10.6 mL, 5.28 mmol) dropwise and the reaction mixture stirred at −78° C. for 5 minutes. The reaction mixture was warmed to 0° C. in a ice/water bath and ethyl bromoacetate (1.20 g, 7.21 mmol) was added dropwise and the mixture stirred at that temperature for 1 hour, and then at room temperature for 2 hours. The reaction mixture was quenched by addition of sat. $NaHCO_3$, diluted with ethyl acetate, and the organic layer was washed with saturated $NaHCO_3$ and then brine. It was dried ($MgSO_4$) and concentrated in vacuo to afford the title compound (1.1 g, 86%) as a yellow solid. Molecular weight (MS): 263.

B. 3,4-Dihydro-2-(2-hydroxyethyl)-6-methoxy-1(2H)-isoquinolinone

A solution of the title A compound (1.2 g, 4.55 mmol) in THF (40 mL) was cooled to −78° C. and 2.0 M LiBH4 in THF (5.00 mL, 10.0 mmol) was added dropwise under a $N_2$ atmosphere. The reaction mixture was warmed to 0° C. and stirred for 2.0 hours, and then stirred at room temperature for another hour. The reaction mixture was cooled in an ice/water bath and quenched by addition of saturated $NaHCO_3$, diluted with ethyl acetate. The organic layer was washed with saturated $NaHCO_3$ and brine. After drying over anhydrous $MgSO_4$, the solvent was evaporated to yield the title compound (645.0 mg, 64% yield) as a white solid. Molecular weight (MS): 222.

C. Methanesulfonic Acid 2-(1,2,3,4-Tetrahydro-6-methoxy-1-oxo-2-isoquinolinyl)ethyl Ester To a solution of the title B compound (300.0 mg, 1.35 mmol) in dry $CH_2Cl_2$ was added triethylamine (282 mL, 2.02 mmol) at −10° C., followed by methanesulfonyl chloride (115 mL, 1.49 mmol) under a $N_2$ atmosphere, and the mixture stirred at that temperature for 35 minutes. The reaction mixture was diluted with dichloromethane and washed with water. The organic layer was separated, dried ($MgSO_4$) and concentrated in vacuo to afford the title compound (316.0 mg, 79%) as a white solid.

D. 3,4-Dihydro-6-methoxy-2-[2-(4-phenyl-1-piperidinyl)-ethyl]-1(2H)-isoquinolinone, Monohydrochloride To a solution of the title C compound (314.0 mg, 1.06 mmol) in $CH_3CN$ was added $K_2CO_3$ (172.0 mg, 1.25 mmol) followed by 4-phenyl piperidine (202.0 mg, 1.25 mmol). The resulting white suspension was stirred at room temperature for 16 hours. The solvent was removed in vacuo and the residue in ethyl acetate was washed with saturated $NaHCO_3$ and brine. It was dried ($MgS_4$) and concentrated in vacuo to yield a yellow solid. The crude product was subjected to silica gel chromatography, eluting with EtOAc:hexane:$Et_3N$ (10:90:1 to 100:0:10) to afford a white solid (320 mg, 70% yield) which was converted to its hydrochloride salt, mp 232–235° C.

Mass spectrum (CI): $(M+H)^+365^+$. Analysis calculated for $C_{23}H_{29}N_2O_2Cl \cdot 0.18H_2O$: C, 68.35; H, 7.32; N, 6.93. Found: C, 68.14; H, 7.37; N, 6.68.

Example 2

6-([1,1'-Biphenyl]-2-ylmethoxy)-3,4-dihydro-2-[2-(4-phenyl-1-piperidinyl)ethyl]-1(2H)-isoquinolinone, Monohydrochloride

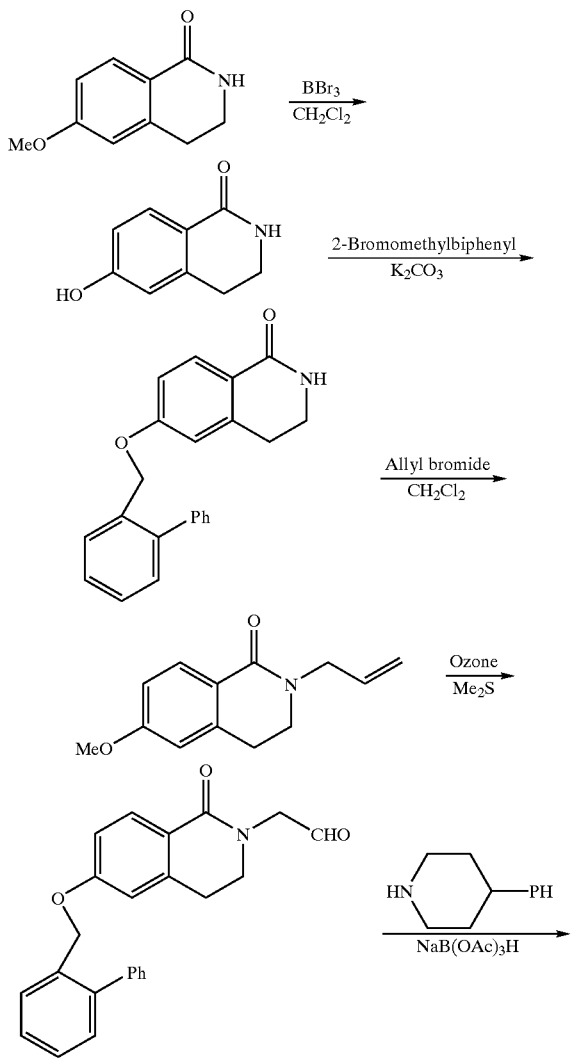

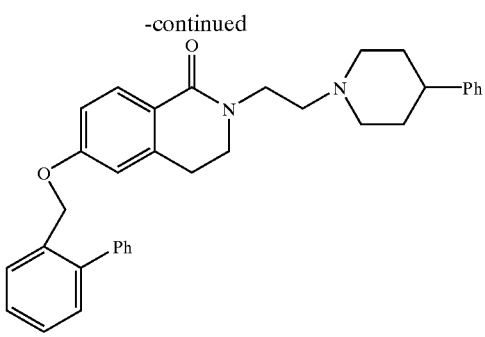

A. 3,4-Dihydro-6-hydroxy-1(2H)-isoquinolinone

To a solution of the title A compound of Example 1 (3.8 g, 21.5 mmol; 3,4-dihydro-6-methoxy-2-[2-(4-phenyl-1-piperidinyl)-ethyl]-1(2H)-isoquinolinone, monohydrochloride) in methylene chloride (50 mL) at −78° C. was added a solution of boron tribromide (1M, 53.7 mL, 53.7 mmol) under nitrogen. The reaction mixture was stirred at for 16 hours, quenched with saturated amminium chloride solution and extracted repeatedly with EtOAc. The organic layer was dried over MgSO$_4$ and concentrated to give the crude product which was triturated with acetone to afford the title compound (2.3 g, 66% yield) as an off-white solid.

B. 6-([1,1'-Biphenyl]-2-ylmethoxy)-3,4-dihydro-1(2H)-isoquinolinone

To a solution of the title A compound (1.85 g, 11.34 mmol) in DMF (40 mL) was added a solution of NaN(Me$_3$Si)$_2$ (1M in THF, 12.5 mL, 12.5 mmol) with stirring at 0° C. under nitrogen. A thick precipitate appeared. The mixture was allowed to come to room temperature and stirred for 15 minutes. The mixture was then cooled to 0° C. followed by the addition of 2-bromomethylbiphenyl (2.07 mL, 11.34 mmol). The reaction mixture was stirred at room temperature for 1.5 hours, diluted with methylene chloride, washed with sat. sodium bicarbonate solution. It was dried (MgSO$_4$) and concentrated to give the title compound as a foam (3.72 g, 100%). Molecular weight (MS): 329.

C. 6-([1,1'-Biphenyl]-2-ylmethoxy)-3,4-dihydro-2-(2-propenyl)-1(2H)-isoquinolinone To a solution of the title B compound (3.72 g, 11.34 mmol) in THF (40 mL) was added a solution of NaN(Me$_3$Si)$_2$ (1M in THF, 12.5 mL, 12.5 mmol) with stirring at −50° C. under nitrogen. A thick precipitate appeared. The mixture was allowed to come to room temperature and stirred for 5 minutes. The mixture was then cooled to −50° C. followed by the addition of allyl bromide (3.92 mL, 45.36 mmol). The reaction mixture was stirred at room temperature for 15 minutes and then diluted with DMF (15 mL). The reaction mixture became homogeneous. It was stirred at room temperature for 1 hour; diluted with EtOAc, washed with sodium bicarbonate and brine. The organic layer was dried (MgSO$_4$) and concentrated to give a yellow. This was subjected to flash chromatography on silica gel (hexane:EtOAc/2:1) to afford the title compound as a pale solid (4 g, 95%). Molecular weight (MS)=369.

D. 6-([1,1'-Biphenyl]-2-ylmethoxy)-3,4-dihydro-1-oxo-2(1H)-isoquinolinacetaldehyde Ozone gas was bubbled through a solution of the title C compound (2 g) in 50 mL methylene chloride at −78° C. until a light blue color was achieved. The excess ozone was purged off with a stream of nitrogen and the reaction mixture was treated with dimethylsulfide (5 mL). The mixture was stirred at room temperature for 3 hours and concentrated. The residue was subjected to flash chromatography (silica gel/hexane-EtOAc 1:2) to give a colorless gummy solid (1.0 g, 50%).

E. 6-([1,1'-Biphenyl]-2-ylmethoxy)-3,4-dihydro-2-[2-(4-phenyl-1-piperidinyl)ethyl]-1(2H)-isoquinolinone, Monohydrochloride To a solution of the title D compound (92.7 mg, 0.25 mmol) and 4-phenylpiperidine (40.2 mg, 0.25 mmol) in THF (1 mL) was added acetic acid (14.3 mL, 0.25 mmol). The mixture was stirred at room temperature for 15 minutes and then sodium triactoxyborohydride (68.9 mg, 0.325 mmol) was added. The resction mixture was stirred at room temperature for 16 hours and diluted with methylene chloride. The solution was washed with saturated sodium bicarbonate solution, dried (magnesium sulfate) and concentrated. The resulting crude product was taken up in methylene chloride, cooled to −78° C. and treated with 4 N HCl in dioxane (0.15 mL). The solution was concentrated and the residue triturated with EtOAc to give the title compound as a white solid (40 mg, 31%). Molecular weight (MS): 516.

Using methodology analogous to that described for the title compound of Example 2, the compounds of Examples 3 and 4 were prepared.

Example 3

(S)-6-([1,1'-Biphenyl]-2-ylmethoxy)-3,4-dihydro-2-[2-[(1-phenylethyl)amino]ethyl]-1(2H)-isoquinolinone, [R-(R*,R*)]-2,3-Dihydroxybutanedioate (1:1)

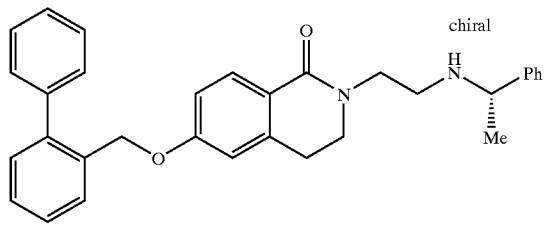

L-Tartrate (1:1 Salt)

MS: (M+H)$^+$477.

Example 4

(R)-6-([1,1'-Biphenyl]-2-ylmethoxy)-3,4-dihydro-2-[2-[(1-phenylethyl)amino]ethyl]-1(2H)-isoquinolinone, [R-(R*,R*)]-2,3-Dihydroxybutanedioate (1:1)

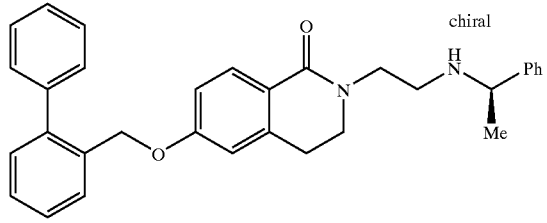

L-Tartrate (1:1 Salt)

MS: (M+H)$^+$477.

Example 5

2,3,4,5-Tetrahydro-7-methoxy-3-methyl-3-[(4-phenyl-1-piperidinyl)methyl]-1H-2-benzazepin-1-one and 1,3,4,5-Tetrahydro-7-methoxy-3-methyl-3-[(4-phenyl-1-piperidinyl)-methyl]-2H-1-benzazepin-2-one

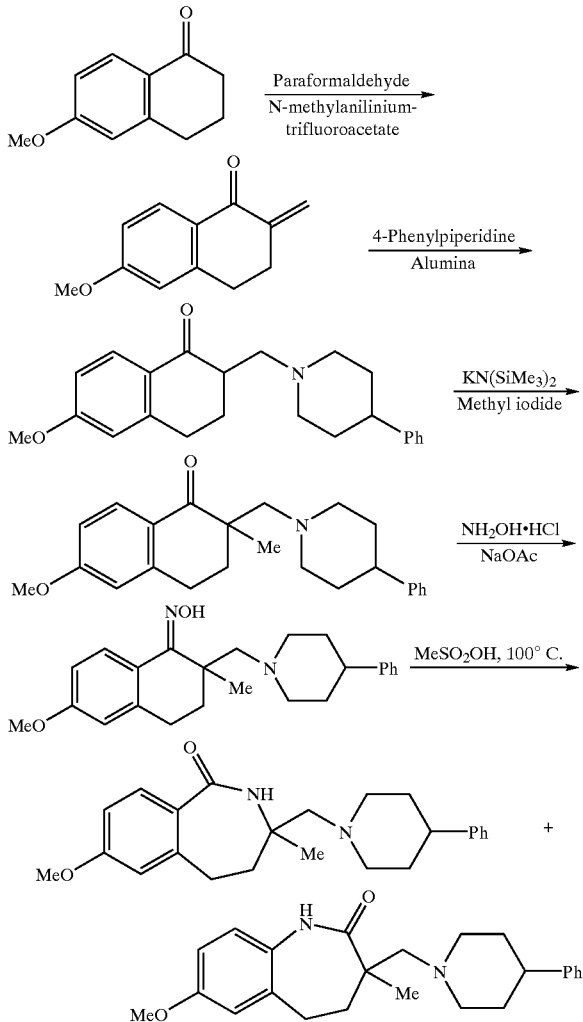

A. 3,4-Dihydro-6-methoxy-2-methylene-1(2H)-naphthalenone

A mixture of 6-methoxytetralone (29.24 g, 165.9 mmol), paraformaldehyde (22.4 g, 746.6 mmol) and N-methylanilinium trifluoroactate (55 g, 248.9 mmol) in 250 mL THF was refluxed for 4 hours and allowed to come to room temperature. To this was added ether (250 mL) with stirring and the mixture was decanted to remove the gummy precipitate. The supernatant was washed with sat. NaHCO$_3$, the oganic layer was dried (MgSO$_4$) and concentrated. The residue was redissolved in ether, filtered through celite and concentrated to afford the title compound as a thick yellow oil.

B. 3,4-Dihydro-6-methoxy-2-[(4-phenyl-1-piperidinyl)-methyl]-1(2H)-naphthalenone, Hydrochloride To a mixture of the title A compound (2.2 g, 12.11 mmol), 4-phenylpiperidine (1.95 g, 12.11 mmol) and alumina (4.56 g) in 300 mL toluene was added water (0.219 mL) and the mixture was stirred at room temperature for 3.5 hours. The reaction mixture was then filtered, the residue washed with ethyl acetate and the combined filtrate was concentrated. The residue was dissolved in dichloromethane, acidified with 4 N HCl in dioxane, concentrated and the residue triturated sequentially with ethyl acetate and acetonitrile to afford the title compound (4.2 g, 90%) as a white solid, mp 176–177° C.

Analysis calculated for C$_{23}$H$_{27}$NO$_2$.HCl: C, 71.58; H, 7.31; N, 3.63. Found: C, 72.08; H, 7.21; N, 3.64.

C. 3,4-Dihydro-6-methoxy-2-methyl-2-[(4-phenyl-1-piperidinyl)methyl]-1(2H)-naphthalenone, Hydrochloride To a solution of the title B compound (379 mg, 1.084 mmol, free base) in THF (10 mL) at −78° C. under nitrogen with stirring was added a solution of KN(SiMe$_3$)$_2$ (0.5 M in toluene, 2.39 mL, 1.19 mmol). The reaction mixture was stirred at −78° C. for 5 minutes followed by the addition of methyl iodide (0.223 mL, 3.58 mmol). The mixture was stirred at −78° C. for another 15 minutes, then kept at −16° C. for 0.5 hours followed by the addition of Et3N (0.832 mL, 5.96 mmol). The mixture was quenched with saturated sodium bicarbonate and extracted with ethyl acetate. The organic layer was washed with brine, dried over magnesium sulfate and concentrated to afford a thick gummy residue. This was converted to its hydrochloride by treatment with hydrochloric to afford the title compound as a white solid, mp 185–186° C.

D. (Z)- and (E)-3,4-Dihydro-6-methoxy-2-methyl-2-[(4-phenyl-1-piperidinyl)methyl]-1(2H)-naphthalenone, Oxime A mixture of the title C compound (2.33 g, 6.41 mmol), hydroxylamine hydrochloride (2.23 g, 32.0 mmol), and sodium acetate (1.89 g, 23.1 mmol) in ethanol (46 mL) was heated at 80° C. in a sealed pressure bottle. The solvent was removed and the residue was partitioned between 1N sodium hydroxide solution and ethyl acetate. The organic layer was washed with saturated sodium chloride solution, dried over sodium sulfate and evaporated in vacuo to obtain 2.15 g of a tan solid. The crude product was purified by chromatography on silica gel eluting with hexane/ethyl acetate (7/3) containing 0.1% triethylamine to obtain 0.26 g (26%) of (Z)-3,4-dihydro-6-methoxy-2-methyl-2-[(4-phenyl-1-piperidinyl)methyl]-1(2H)-naphthalenone, oxime, mp 169–170° C. (Analysis calculated for C$_{24}$H$_{30}$N$_2$O$_2$.0.33H$_2$O: C, 74.96; H, 8.04; N, 7.29. F: C, 75.07; H, 7.95; N, 7.18) and 1.0 g (41%) of (E)-3,4-dihydro-6-methoxy-2-methyl-2-[(4-phenyl-1-piperidinyl)methyl]-1 (2H)-naphthalenone, m.p 174–176° C. Analysis calculated for C$_{24}$H$_{30}$N$_2$O$_2$.0.23H$_2$O: C, 75.32; H, 8.02; N, 7.32. Found: C, 75.38; H, 7.96; N, 7.26).

E. 2,3,4,5-Tetrahydro-7-methoxy-3-methyl-3-[(4-phenyl-1-piperidinyl)methyl]-1H-2-benzazepin-1-one and 1,3,4,5-tetrahydro-7-methoxy-3-methyl-3-[(4-phenyl-1-piperidinyl)methyl]-2H-1-benzazepin-2-one A solution of the title D compound (5.00 g, 13.2 mmol) in methanesulfonic acid (100 mL) containing phosphorus pentoxide (10 g) was heated at 100° C. for 15 minutes. The reaction mixture was cooled to room temperature, poured onto ice, neutralized with solid sodium bicarbonate and extracted with methylene chloride. The extracts were washed with saturated sodium chloride solution, dried over magnesium sulfate and evaporated in vacuo to obtain 4.79 g of a dark brown solid. The crude material was purified by chromatography on silica gel eluting with 4:1 methylene chloride/acetone to obtain 2.29 g of 2,3,4,5-tetrahydro-7-methoxy-3-methyl-3-[(4-phenyl-1-piperidinyl)methyl]-1H-2-benzazepin-1-one (46), mp 127–128° C. (Analysis calculated for C24H30N2O2.0.12H2O: C, 75.73; H, 8.01; N, 7.36. Found: C, 75.73; H, 7.99; N,7.30) and 0.97 g of 1,3,4,5-tetrahydro-7-methoxy-3-[[(4-phenyl-1-piperanzinyl)methyl]-2H-1-benzazepin-2-one (19%), mp 167–169° C.

Example 6

3,4-Dihydro-6-methoxy-3-methyl-3-[(4-phenyl-1-piper-azinyl)-methyl]-1(2H)-isoquinolinone

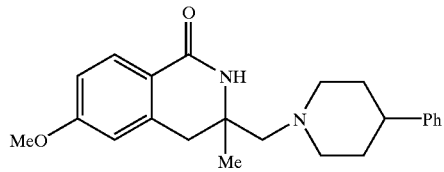

This compound was prepared from the commercially available 5-methoxyindanone by methodology analogous to that described for the title compound of Example 5. The product was obtained as an off-white solid, mp 93–95° C.

Analysis calculated for $C_{23}H_{28}N_2O_2 \cdot 0.55H_2O$: C, 73.79; H, 7.83; N, 7.48. Found: C, 73.80; H, 7.94; N, 7.06.

Example 7

1,2,3,4-Tetrahydro-6-(phenylmethoxy)-2-[2-(4-phenyl-1-piperidinyl)ethyl]-1-isoquinolinemethanol, Dihydrochloride

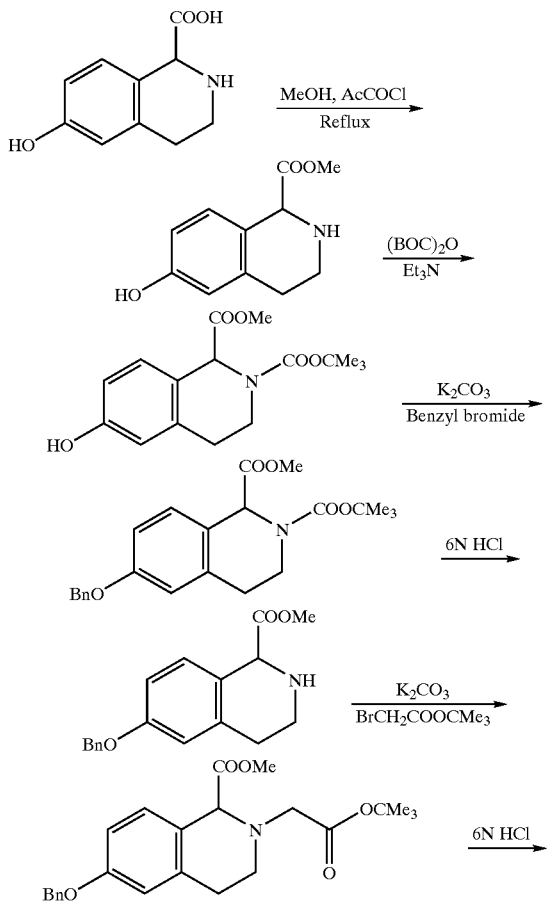

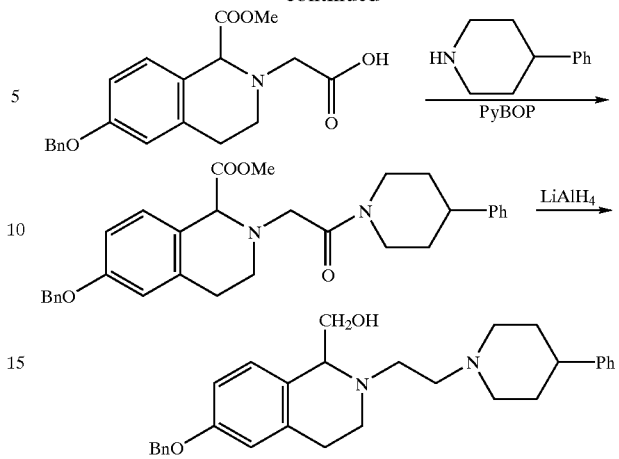

A. 1,2,3,4-Tetrahydro-6-hydroxy-1-isoquinolinecarboxylic Acid Methyl Ester

A suspension of 1,2,3,4-tetrahydro-6-hydroxy-1-isoquinolinecarboxylic acid (5.0 g, 25.9 mmol, prepared according to W. K. Anderson, H. L. McPherson, J. S. New and A. C. Rick, Journal of Medicinal Chemistry, Vol. 27, p. 1321, 1984) in methanol (150 mL) was treated with acetyl chloride (3 mL) (reaction mixture became homogenous) and heated under reflux for 24 hours. The reaction mixture was then cooled to room temperature and concentrated in vacuo. It was diluted with ethyl acetate and washed with saturated sodium bicarbonate solution and water. After drying over anhydrous magnesium sulfate, the solvent was removed in vacuo to yield the title compound (4.0 g, 75%) as a colorless solid, mp 214–216° C.

B. 3,4-Dihydro-6-hydroxy-1,2(1H)-isoquinolinedicarboxylic Acid 1-Methyl 2-(1,1-Dimethylethyl)ester A suspension of the title A compound (5.0 g, 25.9 mmol) in tetrahydrofuran (20 mL) was treated with triethyl amine (3 mL) followed by di-tert-butyl dicarbonate (5.0 g, 25.9 mmol) and stirred at room temperature for 1 hour. The reaction mixture was then diluted with ethyl acetate (100 mL) and washed with 10% citric acid and water. After drying over anhydrous magnesium sulfate, the solvent was removed in vacuo to obtain the title compound (7.0 g, 88%) as an oil.

C. 3,4-Dihydro-6-(phenylmethoxy)-1,2(1H)-isoquinolinedicarboxylic Acid 1-Methyl 2-(1,1-Dimethylethyl)ester A solution of the title B compound (5.0 g, 16.2 mmol) in dimethylformamide (10 mL) was treated with powdered potassium carbonate (9.0 g, 65.2 mmol) followed by benzyl bromide (3.0 g, 18.0 mmol). The reaction mixture was stirred at room temperature for 3 hours, pured water (100 mL) and extracted with ethyl acetate. The combined extracts were washed with water, dried over anhydrous magnesium sulfate and the solvent was evaporated. The residue was purified by flash chromatography on silica gel eluting with a mixture of hexanes and ethyl acetate (9:1) to give the title compound (5.0 g, 77%) as an oil.

D. 1,2,3,4-Tetrahydro-6-(phenylmethoxy)-1-isoquinolinecarboxylic Acid Methyl Ester A solution of the title C compound (3.0 g, 7.5 mmol) in ethyl acetate (10 mL) under argon was treated with 6N hydrochloric acid solution (2 mL) and stirred at room temperature for 24 hours. The reaction mixture was diluted with ethyl acetate and washed with water, sodium bicarbonate and brine. After drying over anhydrous magnesium sulfate, the solvent was evaporated in vacuo to give the title compound (2.0 g, 89%) as an oil. Mass spectrum (M+H)$^+$= 298.

E. 3,4-Dihydro-6-methoxy-3-methyl-3-[(4-phenyl-1-piperidinyl-methyl]-1 (2H)-isoquinol A solution of the title D compound (0.5 g, 1.7 mmol) in acetone (6 mL) was treated with powdered potassium carbonate (1.0 g, 7.2 mmol) followed by tert-butylbromoacetate (0.36 g, 1.8 mmol). The reaction mixture was stirred at room temperature for 3 hours and diluted with ethyl acetate (100 mL). The organic layer was washed with water (50 mL), dried over anhydrous magnesium sulfate and evaporated to give the title compound (0.5 g, 72%) as an oil. Mass spectrum: (M+H)$^+$=412.

F. 3,4-Dihydro-1-(methoxycarbonyl)-6-(phenylmethoxy)-2 (1H)-isoquinolineacetic Acid A solution of the title E compound (2.0 g, 4.9 mmol) in ethyl acetate (10 mL) under argon was treated with 6N hydrochloric acid solution (3 mL) and stirred at room temperature for 24 hours. The reaction mixture was diluted with ethyl acetate and washed with water, sodium bicarbonate and brine. After drying over anhydrous magnesium sulfate, the solvent was vaporated to give the title compound (1.7 g, 98%) as an oil. Mass spectrum M+H)$^+$=356.

G. 1,2,3,4-Tetrahydro-2-[2-oxo-2-(4-phenyl-1-piperidinyl)-ethyl]-6-(phenylmethoxy)-1-isoquinolinecarboxylic Acid, Methyl Ester A mixture of the title compound (0.5 g, 1.4 mmol) and 4-phenylpiperidine (0.30 g, 1.5 mmol) in dichloromethane (5 mL) under argon was treated with diisopropylethyl amine (0.5 g, 4.2 mmol, 0.8 mL) followed by PYBOP (benzotriazole-1-yl-oxy-tris-pyrrolidino-phosphonium hexaflurophosphate) (0.73 g, 1.4 mmol). The reaction mixture was stirred at room temperature for 1 hour; diluted with ethyl acetate and washed with water, sodium bicarbonate and brine. After drying over anhydrous magnesium sulfate, the solvent was evaporated and the residue was purified by flash chromatography on silica gel eluting with a mixture of hexanes/ethyl acetate (1:1) to give the title product (0.2 g, 28%) as a colorless solid, mp 112–114° C. Analysis calculated for $C_{31}H_{34}N_2O_4 \cdot 2H_2O$: C, 74.14; H, 6.90; N, 5.58. Found: C, 74.12; H, 6.74; N, 5.37.

H. 1,2,3,4-Tetrahydro-6-(phenylmethoxy)-2-[2-(4-phenyl-1-piperidinyl)ethyl]-1-isoquinolinemethanol, Dihydrochloride A solution of the title G compound (0.28 g, 0.56 mmol) in tetrahydrofuran (3 mL) under argon was treated with a solution of 1M lithiumaluminum hydride in tetrahydrofuran (0.68 mL, 0.68 mmol). The reaction mixture was stirred at room temperature for 1 hour, quenched with slow addition of water (1 mL) and diluted with ethyl acetate. The organic layer was washed with water and brine. After drying over anhydrous magnesium sulfate, the solvent was evaporated and the residue was purified by flash chromatography on silica gel eluting with 5% methanol in dichloromethane to give the title compound (90 mg, 49%). The product was treated with ethereal hydrochloric acid in ethyl ether to provide 1,2,3,4-tetrahydro-6-(phenylmethoxy)-2-[2-(4-phenyl-1-piperidinyl)ethyl]-1-isoquinolinemethanol, dihydrochloride as a colorless solid, mp 205–210° C. (decomposition).

Analysis calculated for $C_{30}H_{36}N_2O_2 \cdot 2HCl \cdot 0.7H_2O$: C, 66.46; H, 7.32; N, 5.17. Found: C, 66.45; H, 7.16; N, 5.

Example 8

3-(2,2-Dimethylpropyl)-3,4-dihydro-6-(hexyloxy)-1 (2H)-isoquinolinone.

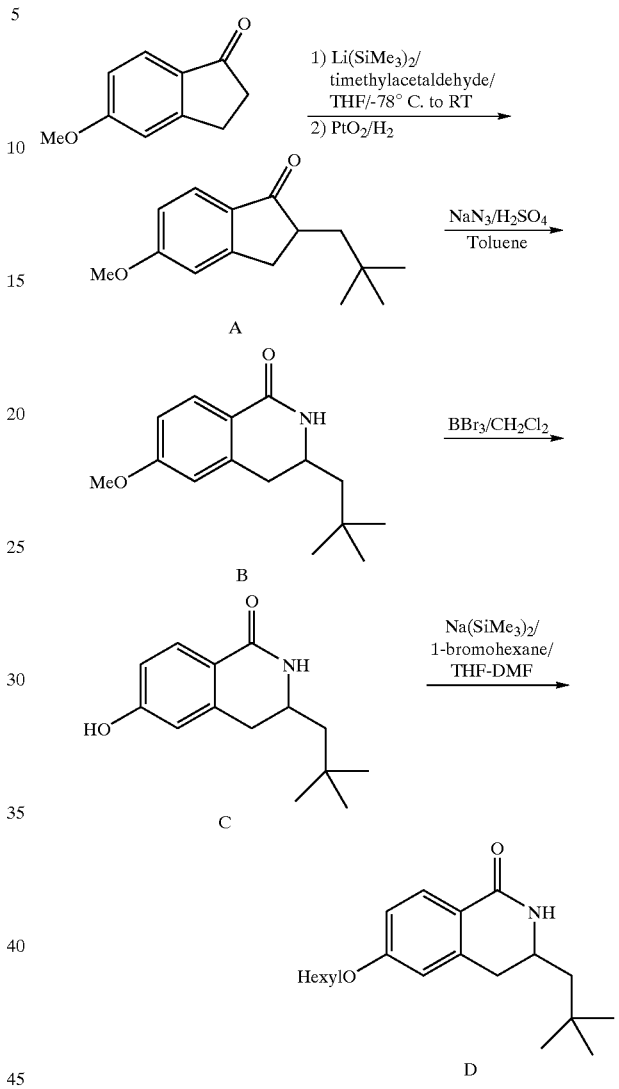

A. Compound A

To a solution of 6-methoxytetralone (11 g, 62.5 mmol) in 200 mL THF was added 1M lithium bistrimethylsilylamide in hexane (65.6 mL, 65.6 mmol) with stirring at −78° C. under nitrogen. The recation mixture was allowed to warm up to room temperature, cooled to −78° C. followed by the addition of trimethylacetaldehyde (5.91 g, 68.9 mmol). The mixture was allowed to come to room temperature and stirred for 15 hours. The reaction mixture was then diluted with ethyl acetate and washed with saturated ammonium chloride solution. The organic layer layer was dried over magnesium sulfate and concentrated. The resulting crude product was taken in EtOH (200 mL), treated with 1 g platinum oxide and stirred under hydrogen atmosphere for 24 hours. To the reaction mixture was added p-toluenesulfonic acid monohydrarte (220 mg) and the strinng was continued for additional 48 h under hydrogen atmosphere. The mixture was filtered through celite, concentrated and the residue subjected to flash chromatography (silica gel/hexane-ethyl acetate 9:1) to give 6.4 g of compound A as a white solid.

B. Compound B

To a reaction mixture containing compound A (6.25 g, 25.41 mmol) in toluene (54 mL) and conc. sulfuric acid was added sodium azide (2.064 g, 31.8 mmol) in small portions at 65° C. over 40 minutes. The mixture was stirred at 65° C. for 1.5 h, decanted and the top layer was discarded. The lower dark colored layer was poured over crushed ice and excess saturated sodium bicarbonate solution. The mixture was extracted with methylene chloride, the organic layer was dried over magnesium sulfate, concentrated and the residue subjected to flash chromatography (silica gel/hexane-ethyl acetate 1:1) to afford 3.95 g of dark green solid. This was triturated twice with hot hexane to afford compound B as an off-white solid (2.6 g).

C. Compound C

To a solution of compound B (2.45 g, 9.39 mmol) in 20 mL methylene chloride at −78° C. with stirring was added a 1M solution of boron tribromide in methylene chloride (23.5 mL, 23.5 mmol) over 5 minutes. The mixture was allowed to come to room temperature, stirred for 3.5 h, quenched by adding to ice cold saturated ammonium chloride solution and extracted with ethyl acetate. The organic layer was dried over magnesium sulfate, concentrated, and the residue triturated with 5:1 hexane-ether to afford compound C as an off-white solid (2.3 g).

D. Compound D

A 1M solution of sodium bistrimethylsilylamide in hexane (0.425 mL, 0.425 mmol) was added to a stirred solution of compound C (0.1 g, 0.405 mmol) in 1 mL DMF at 0° C. under nitrogen. The reaction mixture was allowed to come to room temperature, treated with 1-bromohexane (0.0625 mL, 0.446 mmol) and stirred for 12 hours. The mixture was diluted with methylene chloride, washed with saturated sodium bicarbonate solution, the organic layer dried (magnesium sulfate) and concentrated. The crude product was recrystallized from DMF to afford 100 mg of the title compound as a white crystalline solid, m/e 317.

Example 9

3-(2,2-Dimethylpropyl)-8-(hexyloxy)-2,3,4,5-tetrahydro-1H-2-benzazepin-1-one and 3-(2,2-Dimethylpropyl)-8-(hexyloxy)-1,3,4,5-tetrahydro-1H-1-benzazepin-2-one

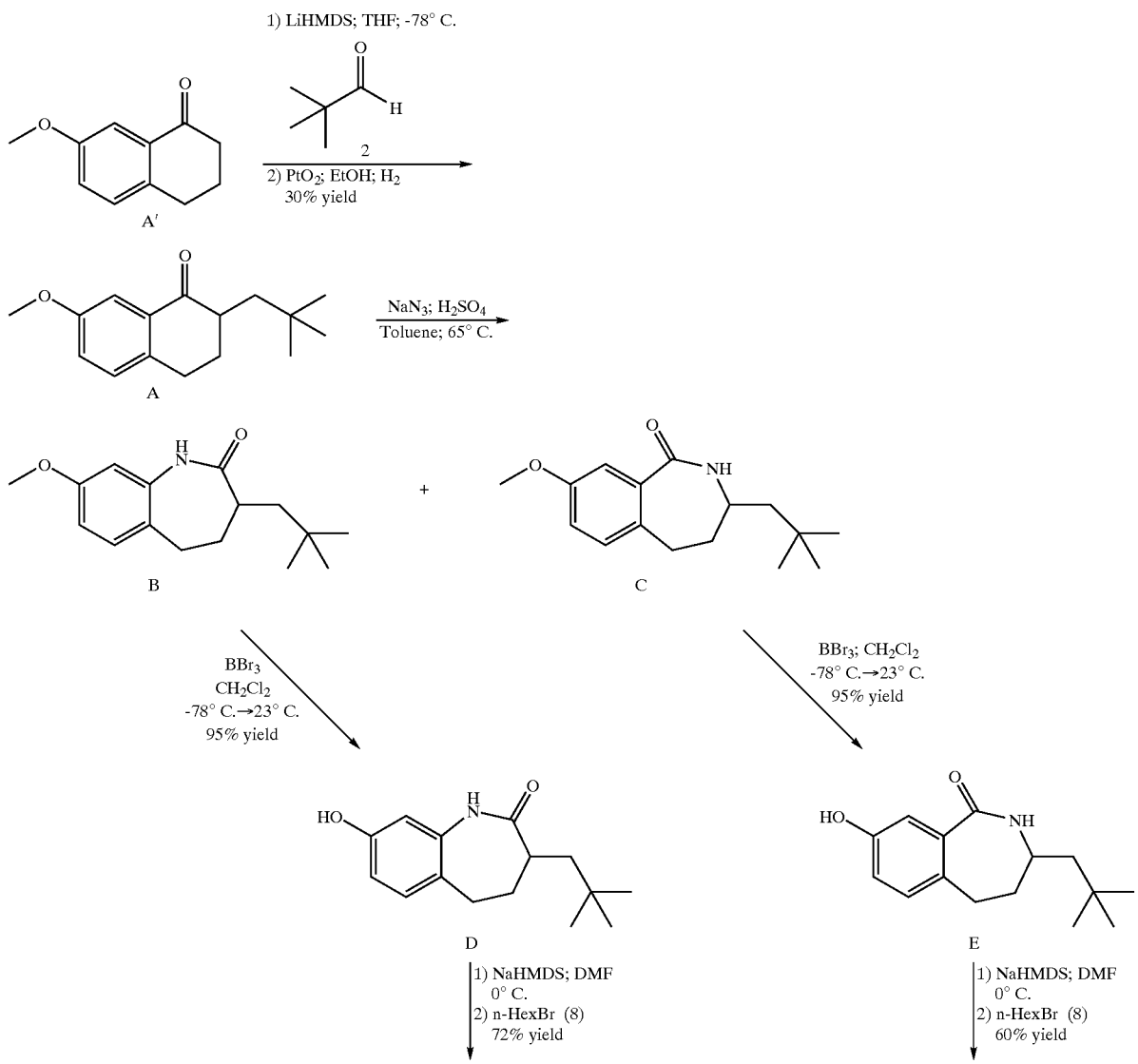

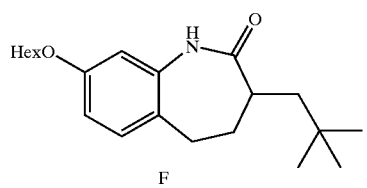 F

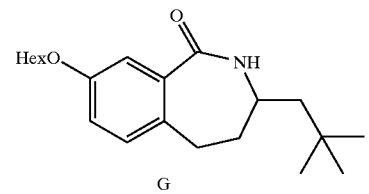 G

A. Compound A

To a solution of compound A' (10 g, 56.7 mmol) in dry THF (200 mL) at −78° C. was added 1M lithium bistrimethylsilylamide (59.6 mL, 59.6 mmol) over 5 minutes while stirring under argon. The stirring was continued at room temperature for 30 minutes and the reaction mixture was cooled to —78° C. and 2,2-dimethyl-acetaldehyde (6.78mL, 62.4 mmol) was added. After the addition, the bath was removed and the reaction was stirred at room temperature for 18 hours. The reaction was diluted with ethyl acetate and washed with saturated ammonium chloride solution. The layers were separated and the aqueous layer was backwashed with ethyl acetate. The combined organic layers were dried ($MgSO_4$), filtered and concentrated in vacuo to yield a dark brown oil. To this material in ethanol (200 mL) was added platinum oxide (1.45 g) and the reaction was stirred under hydrogen (balloon) for 48 hours at room temperature. The resulting mixture was filtered through a celite pad and the cake was washed several times with hot ethanol. The solvent was removed in vacuo to afford a brown heavy oil which was purified by flash chromatography on silica gel (hexanes) to give compound A as a clear heavy oil (4.18 g, 17 mmol, 30% yield. [Mass Spectrum (ESI): $(M+H)^+247^+$].

B. Compounds B and C

To a stirred solution of compound A (3.5 g, 14.2 mmol) in toluene (30 mL) at 65° C. was added rapidly sulfuric acid (7.2 mL, 142 mmol) followed by the addition of sodium azide (1.15 g, 17.8 mmol) in small portions during 4 minutes. The reaction continued to stir for an additional 10 minutes at 65° C. The reaction mixture was cooled to room temperature and the top layer (clearer) was decanted and the bottom (dark and viscous layer) was poured over ice and basicified to pH 8 with saturated sodium bicarbonate. This mixture was extracted with ethyl acetate and the combined extracts were dried ($MgSO_4$) and concentrated in vacuo to yield compounds B and C as a mixture of isomers. Purification by flash chromatography on silica gel using 10% ethyl acetate in hexanes gave compound B (1.146 g, 31%) as a white solid, mp 169–171° C. Analysis calculated for $C_{16}H_{23}NO_2 \cdot 0.273H_2O$: C, 72.17; H, 8.91; N, 5.26 Found: C, 72.17; H, 8.63; N, 5.1. Also recovered from the column was compound C (1.64 g, 44%) as a colorless solid, mp 183–184° C. Analysis calculated for $C_{16}H_{23}NO_2 \cdot 0.00H_2O$: C, 73.33; H, 8.88; N, 5.34. Found: C, 73.33; H, 9.07; N, 5.46.

C. Compounds D and E

To a solution of compound B (824 mg, 3.15 mmol) in dichloromethane (5 mL) at −78° C. was added dropwise 1.0M boron tribromide in dichloromethane (7.88 mL, 7.88 mmol) while stirring under Argon. The bath was removed and the reaction was stirred for 1 hour at room temperature. The reaction was quenched with saturated ammonium chloride and diluted with ethyl acetate. The layers were separated and the aqueous layer was backwashed with fresh ethyl acetate (twice). The organic layers were dried over $MgSO_4$, filtered and concentrated in vacuo to afford compound D as an off-white foam (0.743 g, 95%). Mass Spectrum (ESI): $(M+H)^+248^+$; $(M-H)^-246^-$).

Preparation of Compound E

For the synthesis of compound E, see procedure above for compound D. Compound E was a white foam (HPLC 95% purity @7.92 min; Mass Spectrum (ESI): $(M+H)^+248^+$).

D. Compound F: 3-(2,2-Dimethylpropyl)-8-(hexyloxy)-1,3,4,5-tetrahydro-1H-1-benzazepin-2-one To a solution of compound D (675 mg, 2.73 mmol) in dry DMF (10 mL) at 0° C. was added dropwise 1M sodium hexamethyldisilazide (2.87 mL, 2.87 mmol). The bath was removed and the reaction was stirred under argon at room temperature. To the resulting solution was added alkyl bromide (71 μL, 0.50 mmol) and the reaction mixture was stirred for 18 hours. The crude product was precipitated from the reaction mixture by adding a few drops of water while continuing to stir. The product was purified by flash chromatography on silica gel using 10% ethyl acetate in hexanes to provide compound F as a colorless solid, mp 93–95° C. Analysis calculated for $C_{21}H_{33}NO_2 \cdot 0.045H_2O$: C, 75.90; H, 10.04; N, 4.22. Found: C, 75.90; H, 9.99; N, 4.65.

Compound G: 3-(2,2-Dimethylpropyl)-8-(hexyloxy)-2,3,4,5-tetrahydro-1H-2-benzazepin-1-one was prepared from compound E by the same procedure as described for the synthesis of compound F from D. Compound G was obtained as a white solid, mp 130–131° C. Analysis calculated for $C_{21}H_{33}NO_2 \cdot 0.053H_2O$: C, 75.87; H, 10.04; N, 4.21. Found: C, 75.87; H, 10.24; N, 4.03.

Using the procedures described in Examples 8 and 9, the following were prepared.

| Examples | Structure | Characterization |
|---|---|---|
| 10 | ![structure] | $C_{21}H_{33}NO_2$<br>m/e 331<br>white crystalline solid |

-continued
| Examples | Structure | Characterization |
|---|---|---|
| 11 | 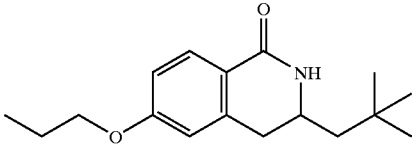 | C₁₇H₂₅NO₂<br>m/e 275<br>white crystalline solid |
| 12 | 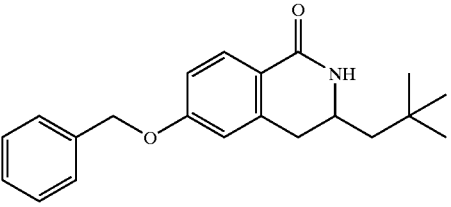 | C₂₁H₂₅NO₂<br>m/e 323<br>off-white solid |
| 13 | 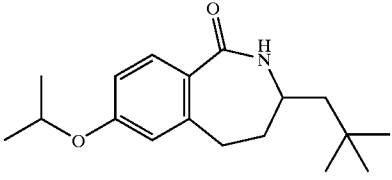 | C₁₈H₂₇NO₂<br>m/e 289<br>white foamy solid |
| 14 | 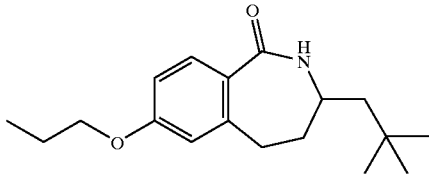 | C₁₈H₂₇NO₂<br>m/e 289<br>white crystalline solid |
| 15 | 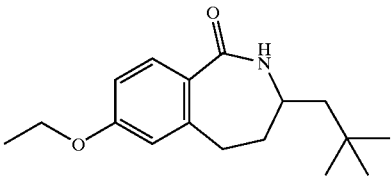 | C₁₇H₂₅NO₂<br>m/e 275<br>white crystalline solid |
| 16 | 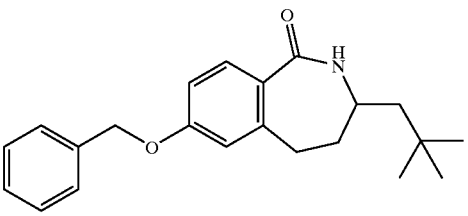 | C₂₂H₂₇NO₂<br>m/e 337<br>white solid |
| 17 | 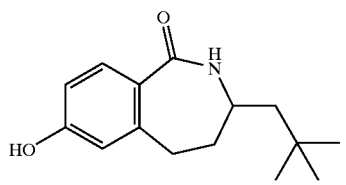 | C₁₅H₂₁NO₂<br>m/e 247<br>off-white solid |

-continued

| Examples | Structure | Characterization |
|---|---|---|
| 18 | 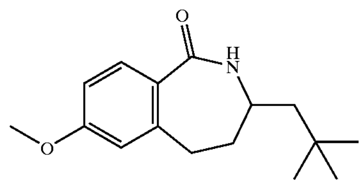 | $C_{16}H_{23}NO_2$<br>m/e 261<br>off-white solid |
| 19 | 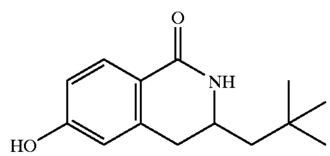 | $C_{14}H_{19}NO_2$<br>m/e 233<br>Pinkish solid |
| 20 | 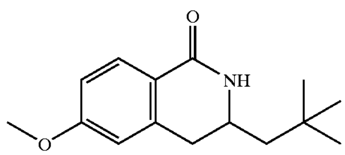 | $C_{15}H_{21}NO_2$<br>m/e 247<br>light yellow crystalline solid |
| 21 | 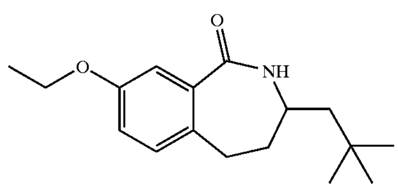 | $C_{17}H_{25}NO_2$<br>Analysis Calculated:<br>C, 74.14; H, 9.15; N, 5.09<br>Found: C, 73.88; H, 9.21; N, 5.01<br>m/e 275<br>white solid; mp 159–160° C. |
| 22 | 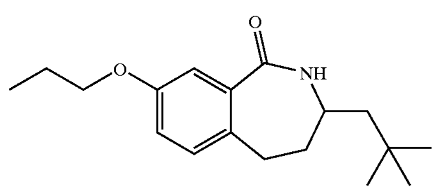 | $C_{18}H_{27}NO_2$<br>Analysis Calculated:<br>C, 74.70; H, 9.40; N, 4.84<br>Found; C, 74.42; H, 9.55; N, 4.63<br>m/e 289<br>white solid; mp 132–133° C. |
| 23 | 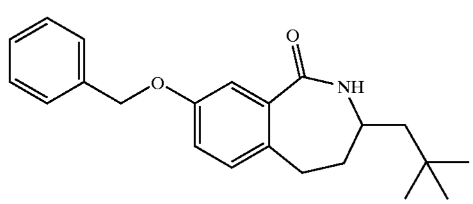 | $C_{22}H_{27}NO_2$<br>m/e 337<br>white solid; mp 142–143° C. |
| 24 | 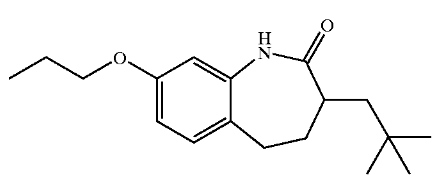 | $C_{18}H_{27}NO_2$<br>m/e 289<br>white solid; mp 117–119° C. |
| 25 | 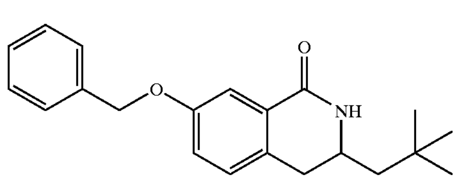 | $C_{21}H_{25}NO_2$<br>m/e 323<br>white solid; mp 139–140° C. |

-continued

| Examples | Structure | Characterization |
|---|---|---|
| 26 | 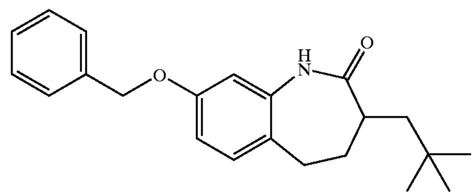 | $C_{22}H_{27}NO_2$<br>m/e 337<br>white solid; mp 150–151° C. |
| 27 | 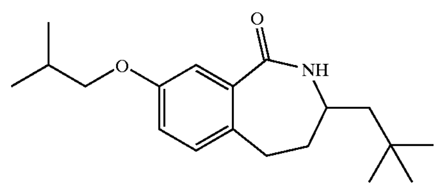 | $C_{19}H_{29}NO_2$<br>m/e 303<br>white solid; mp 148–149° C. |
| 28 | 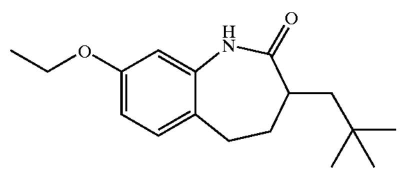 | $C_{17}H_{25}NO_2$<br>m/e 275<br>white solid; mp 136–138° C. |
| 29 | 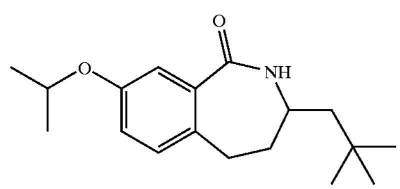 | $C_{18}H_{27}NO_2$<br>Analysis Calculated;<br>C, 74.70; H, 9.40; N, 4.84<br>Found: C, 74.42; H, 9.49;<br>N, 4.62<br>m/e 289<br>white solid; mp 113–114° C. |
| 30 | 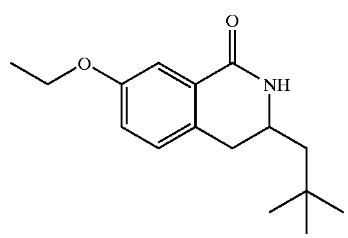 | $C_{16}H_{23}NO_2$<br>m/e 261<br>white solid; mp 129–130° C. |
| 31 | 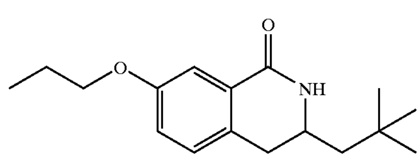 | $C_{17}H_{25}NO_2$<br>m/e 275<br>white solid; mp 88–90° C. |
| 32 | 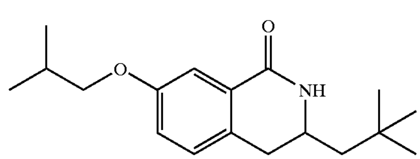 | $C_{18}H_{27}NO_2$<br>m/e 289<br>white solid; mp 142–143° C. |
| 33 | 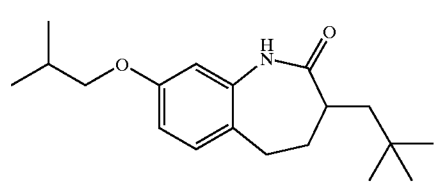 | $C_{19}H_{29}NO_2$<br>m/e 303<br>white solid; mp 139–140° C. |

| Examples | Structure | Characterization |
|---|---|---|
| 34 | 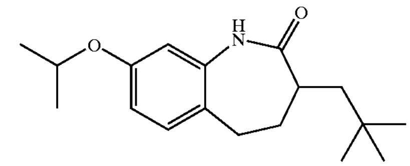 | $C_{18}H_{27}NO_2$<br>m/e 289<br>white solid; mp 132–134° C. |
| 35 | 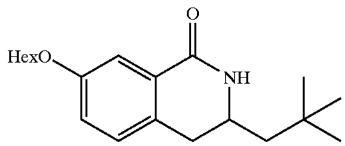 | $C_{20}H_{31}NO_2$<br>m/e 317<br>off-white solid; mp 84–86° C. |
| 36 | 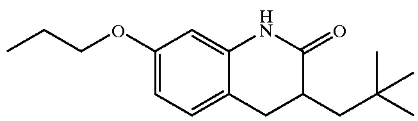 | $C_{17}H_{25}NO_2$<br>m/e 275<br>white solid; mp 109–110° C. |
| 37 | | $C_{17}H_{25}NO_2$<br>m/e 275<br>white solid; mp 135–136° C. |
| 37 | | $C_{15}H_{21}NO_2$<br>m/e 247<br>light tan solid; mp 118–119° C. |
| 38 | 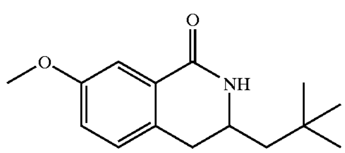 | $C_{15}H_{21}NO_2$<br>m/e 247<br>light tan solid; mp 113–114° C. |
| 39 | 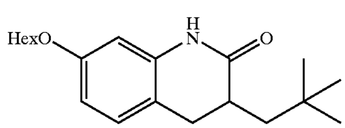 | $C_{20}H_{31}NO_2$<br>m/e 317<br>off-white solid; mp 80–81° C. |

What is claimed is:

1. A method of treating cardiac arrhythmia which comprises administering to a mammal in need thereof an effective amount of a compound of the formula

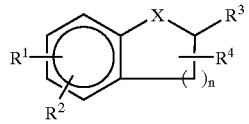

wherein

X is —C(=O)NR$^{3'}$;

R$^1$ is halo, alkyl, cycloalkyl, alkyl(cycloalkyl), aryl, (aryl)alkyl, (aryl)alkenyl, (aryl)alkynyl, O-alkyl, O-alkenyl, O-aryl, O-alky(aryl), O-alkyl(heterocyclo), COO-alkyl, CO-alkyl, CO-amino, CO-substituted amino, alkyl-CO-amino, alkyl-CO-substituted amino, NHCO-alkyl, NHCO-aryl, NHCO-alkyl(aryl), NHCO-alkyl(heterocyclo), N(alkyl)CO-alkyl, N(alkyl)CO-aryl, N(alkyl)CO-heterocyclo, N(alkyl)CO-alkyl(aryl) or N(alkyl)CO-alkyl(heterocyclo);

R$^2$ is hydrogen, alkyl, halo, aryl, (aryl)alkyl, O-alkyl, amino or substituted amino;

R$^3$ and R$^{3'}$ are the same or different and are independently selected from hydrogen, alkyl and alkyl(aryl);

R$^4$ is alkyl-(amino) or alkyl-(NZ$^1$Z$^2$), wherein Z$^1$ and Z$^2$ are taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl or 4-diarylalkyl-1-piperazinyl, optionally substituted with alkyl, alkoxy, alkylthio, halo, aryl or hydroxy; and n is two.

2. The method as recited in claim 1 herein a compound of formula I is administered where $R^1$ is O-alkyl;

$R^2$ is hydrogen; and $R^4$ is alkyl-($NZ^1Z^2$), wherein $Z^1$ and $Z^2$ are taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl or 4-diarylalkyl-1-piperazinyl, optionally substituted with alkyl, alkoxy, alkylthio, halo, aryl or hydroxy.

3. The method as recited in claim 1 wherein the compound of formula I is 2,3,4,5-tetrahydro-7-methoxy-3-methyl-3-[(4-phenyl-1-piperidinyl)methyl]-1H-2-benzazepin-1-one or a pharmaceutically acceptable salt thereof.

* * * * *